US012310555B2

(12) United States Patent
Levy et al.

(10) Patent No.: US 12,310,555 B2
(45) Date of Patent: *May 27, 2025

(54) ENDOSCOPE SYSTEM WITH MULTIPLE CONNECTION INTERFACES TO INTERFACE WITH DIFFERENT VIDEO DATA SIGNAL SOURCES

(71) Applicant: EndoChoice, Inc., Alpharetta, GA (US)

(72) Inventors: Idan Levy, Hadera (IL); Roei Atias, Kiryat Ata (IL); Golan Salman, Atlit (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,865

(22) Filed: Apr. 28, 2023

(65) Prior Publication Data
US 2023/0263371 A1 Aug. 24, 2023

Related U.S. Application Data

(63) Continuation of application No. 17/223,847, filed on Apr. 6, 2021, now Pat. No. 11,672,407, which is a
(Continued)

(51) Int. Cl.
A61B 1/00 (2006.01)
A61B 1/015 (2006.01)
(Continued)

(52) U.S. Cl.
CPC ...... A61B 1/00124 (2013.01); A61B 1/00006 (2013.01); A61B 1/00011 (2013.01);
(Continued)

(58) Field of Classification Search
CPC ............ A61B 1/00124; A61B 1/00006; A61B 1/00126; A61B 1/00128; A61B 1/00165;
(Continued)

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Notice of Allowance dated Apr. 18, 2017 for U.S. Appl. No. 13/713,449.
(Continued)

Primary Examiner — Timothy J Neal
(74) Attorney, Agent, or Firm — Bookoff McAndrews PLLC

(57) ABSTRACT

Endoscopes having a tip section with viewing elements coupled to a CMOS image sensor and/or a CCD image sensor for transforming light captured by the viewing element into digital and/or analog signals are described. A main connector is coupled with the tip section for transmitting the signals to a main control unit of the endoscope. The main connector includes a pad for transmitting digital signals provided by the CMOS image sensor to a push pin probe in a receptacle of the main control unit. The main connector also include another interface for transmitting analog signals to the main control unit.

20 Claims, 7 Drawing Sheets

Related U.S. Application Data continuation of application No. 15/602,411, filed on May 23, 2017, now Pat. No. 10,993,605.

(60) Provisional application No. 62/352,898, filed on Jun. 21, 2016.

(51) Int. Cl.
 *A61B 1/045* (2006.01)
 *A61B 1/05* (2006.01)
 *G02B 23/24* (2006.01)

(52) U.S. Cl.
 CPC ...... *A61B 1/00126* (2013.01); *A61B 1/00128* (2013.01); *A61B 1/00165* (2013.01); *A61B 1/015* (2013.01); *A61B 1/045* (2013.01); *A61B 1/051* (2013.01); *A61B 1/053* (2013.01); *G02B 23/2476* (2013.01); *A61B 1/00059* (2013.01); *A61B 1/05* (2013.01)

(58) Field of Classification Search
 CPC ......... A61B 1/015; A61B 1/045; A61B 1/051; A61B 1/053; A61B 1/00011
 See application file for complete search history.

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,348,035 B1 | 2/2002 | Takami |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 10,993,605 B2 * | 5/2021 | Levy .................. A61B 1/00124 |
| 11,672,407 B2 * | 6/2023 | Levy ...................... A61B 1/045 |
| | | 600/110 |

(56) References Cited

U.S. PATENT DOCUMENTS

| | | |
|---|---|---|
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0125606 A1 | 7/2003 | Amling et al. |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0134997 A1 | 6/2006 | Curtis et al. |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0265498 A1 | 11/2007 | Ito |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0209811 A1 | 8/2009 | Higuchi |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0015833 A1 | 1/2010 | Laughlin et al. |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh et al. |

(56) References Cited

U.S. PATENT DOCUMENTS

| | | |
|---|---|---|
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0035550 A1 | 2/2013 | Watanabe et al. |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0275763 A1 | 9/2014 | King et al. |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 1647543 A | 7/2005 |
| CN | 101043113 A | 9/2007 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1 652 464 A1 | 5/2006 |
| EP | 1690497 | 8/2006 |
| EP | 1835844 | 9/2007 |
| EP | 1968425 | 9/2008 |
| EP | 1986541 | 11/2008 |

(56) References Cited

FOREIGN PATENT DOCUMENTS

| | | |
|---|---|---|
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | S6443227 A | 2/1989 |
| JP | H1043129 | 2/1998 |
| JP | H10239740 | 9/1998 |
| JP | H11103471 A | 4/1999 |
| JP | 11137512 | 5/1999 |
| JP | 2000092478 A | 3/2000 |
| JP | 2003334163 A | 11/2003 |
| JP | 2004236738 A | 8/2004 |
| JP | 2005253543 | 9/2005 |
| JP | 2006025888 | 2/2006 |
| JP | 2006068109 | 3/2006 |
| JP | 2007160123 A | 6/2007 |
| JP | 2007209656 A | 8/2007 |
| JP | 2009000334 A | 1/2009 |
| JP | 2010005180 A | 1/2010 |
| JP | 2010136764 A | 6/2010 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2011052408 | 5/2011 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, Sep. 25, 2014.
International Search Report for PCT/US14/38094, Nov. 6, 2014.
International Search Report for PCT/US2014/037526, Oct. 16, 2014.
International Search Report for PCT/US2014/071085, mailed on Mar. 27, 2015.
International Search Report for PCT/US2014/58143, mailed on Jan. 21, 2015.
International Search Report for PCT/US2015/012506, mailed on Dec. 11, 2015.
International Search Report for PCT/US2015/012751, mailed on Jun. 26, 2015.
International Search Report for PCT/US2015/027902, mailed on Jul. 23, 2015.
International Search Report for PCT/US2015/28962, mailed on Jul. 28, 2015.
International Search Report for PCT/US2015/29421, mailed on Aug. 7, 2015.
International Search Report for PCT/US2015/41396, mailed on Sep. 29, 2015.

(56) References Cited

OTHER PUBLICATIONS

International Search Report for PCT/US2015/47334, mailed on Dec. 28, 2015.
International Search Report for PCT/US2015/6548, mailed on Feb. 26, 2016.
International Search Report for PCT/US2015/66486, mailed on Dec. 17, 2015.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action date Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastics Technology, June 2001—article obtained online from http://www.otonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Ocotber 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action mailed Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Japanese Office Action in corresponding Japanese Application No. 2021-209619, dated Jan. 4, 2023 (3 pages).

* cited by examiner

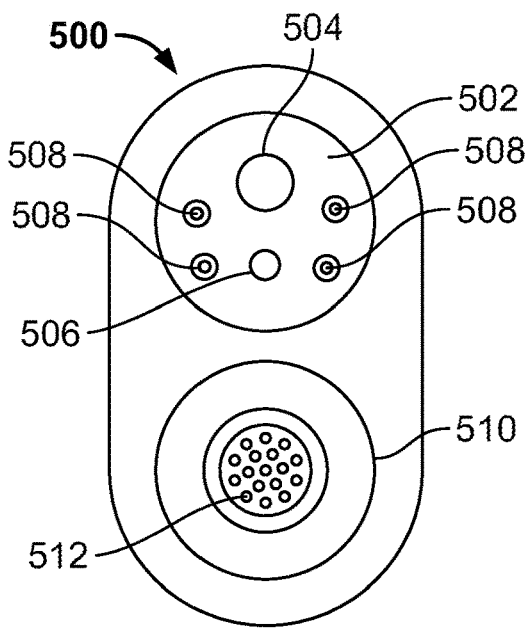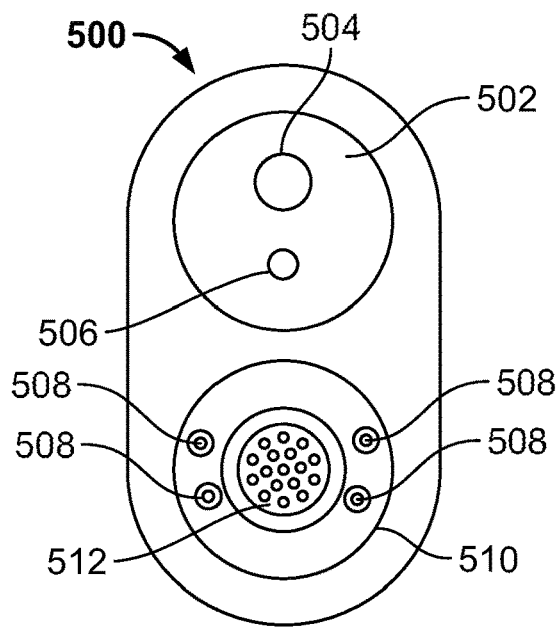
FIG. 5A          FIG. 5B
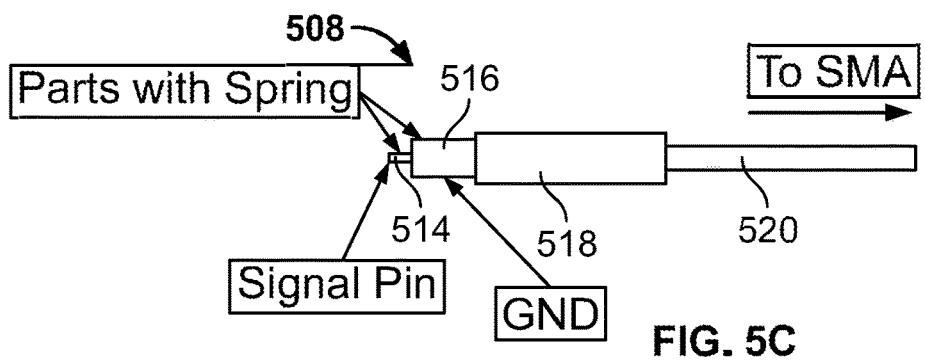
FIG. 5C
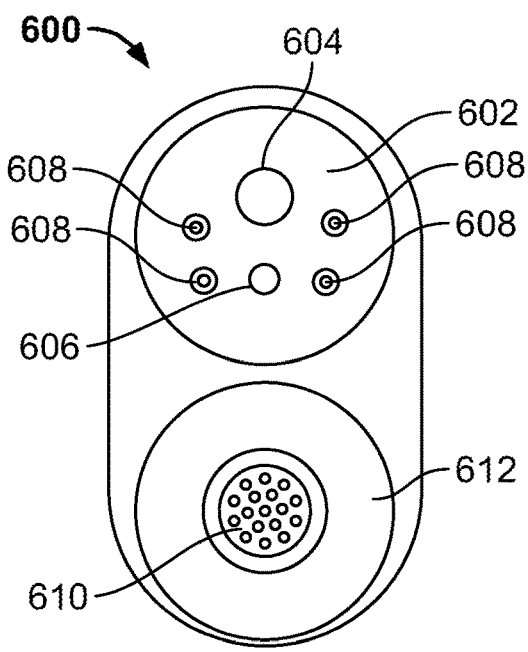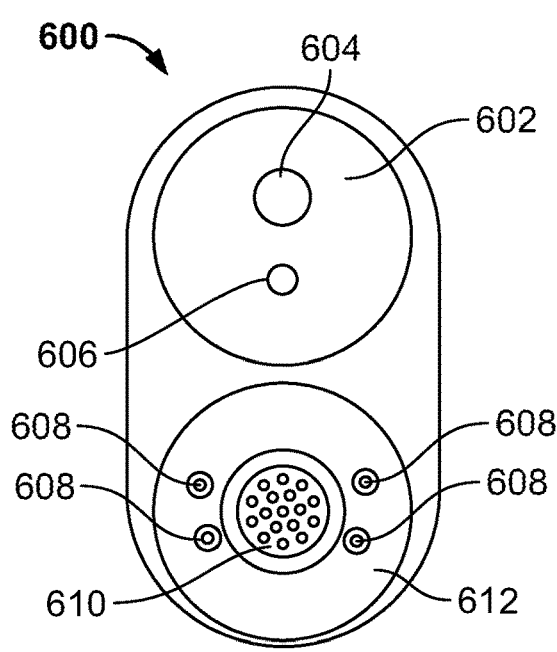
FIG. 6A          FIG. 6B

ENDOSCOPE SYSTEM WITH MULTIPLE CONNECTION INTERFACES TO INTERFACE WITH DIFFERENT VIDEO DATA SIGNAL SOURCES

CROSS-REFERENCE

This application is a continuation of U.S. Nonprovisional patent application Ser. No. 17/223,847, filed April 6, 2021, which is a continuation of U.S. Nonprovisional patent application Ser. No. 15/602,411 filed May 23, 2017, now U.S. Pat. No. 10,993,605, which claims the benefit of U.S. Provisional Patent Application No. 62/352,898, filed Jun. 21, 2016, the entireties of all of which are incorporated herein by reference.

The present application relates to U.S. patent application Ser. No. 14/468,189, which has been assigned U.S. Patent Publication Number 20150057500, entitled "System for Connecting and Disconnecting A Main Connector and a Main Control Unit of An Endoscope", filed on Aug. 26, 2014, which in turn relies on U.S. Patent Provisional Application No. 61/870,144, of the same title, and filed on Aug. 26, 2013 and U.S. Patent Provisional Application No. 61/968,436, of the same title, and filed on Mar. 21, 2014, for priority.

The above-listed applications are herein incorporated by reference in their entirety.

FIELD

The present specification relates generally to endoscopes, and more specifically, to a main control unit for detecting and responding to different types of image sensors positioned within an endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

Some endoscopes have viewing elements for viewing an internal organ, such as the colon, and an illuminator for illuminating the field of view of the viewing elements. The viewing elements and illuminators are located in a tip of the endoscope and are used to capture images of the internal walls of the body cavity being endoscopically scanned. The captured images are sent to a control unit coupled with the endoscope via one of the channels present in the scope shaft, for being displayed on a screen coupled with the control unit. During an endoscopic procedure, an operating physician guides the endoscope within a patient's body by using the captured images displayed on the screen coupled with the control unit as a guide.

Endoscopes capture images of internal organs by means of one or more viewing elements such as cameras placed in a tip portion. Each viewing element is coupled with an image sensor to transform that light captured by the viewing element into at least one image. Image sensors may be Charged Coupled Devices (CCD's) or Complementary Metal Oxide Semiconductor (CMOS) image sensors, or other suitable devices having a light sensitive surface usable for capturing an image. Signals such as analog signals or digital signals generated by the image sensors are transmitted to a main control unit via a main connector of the endoscope for display on a screen coupled with the main control unit. CCD based endoscopes are fitted with main connectors having a push/pull electric connector, such as a LEMO® connector, which are commonly known in the art. A LEMO® connector fits into a corresponding LEMO® connector interface provided on a main control unit of the endoscope for transmission of the analog image signals having a bandwidth of ⅓ GHz. However, CMOS image sensors generate digital image/video signals having a bandwidth of the order of 1.5 GHz or more which is very high compared to signals generated by the CCD image sensors, and, as a result cannot be transmitted via a standard LEMO® interface.

There is a therefore a need for a main control unit interface and/or adapter that can support both CCD-based and CMOS-based main connector fittings in endoscopes.

What is also needed is a high-speed transmission interface that maintains signal integrity and does not result in signal distortion that can be employed with CMOS-based endoscopes.

SUMMARY

The present specification discloses an endoscope system comprising: an endoscope comprising a tip section having at least one viewing element; a main connector coupled with the tip section and configured to receive and transmit a first set of video data signals from the at least one viewing element wherein the main connector comprises at least one pad; and a control unit comprising a receptacle positioned on an exterior surface of the control unit and configured to receive the main connector, wherein the receptacle has a first region, wherein the first region comprises at least one probe, wherein said at least one probe comprises a spring loaded pin, and wherein, upon attachment of the main connector to said receptacle, the at least one probe abuts the at least one pad such that the at least one probe is compressed.

Optionally, the at least one pad is planar and metallic.

Optionally, the first region comprises a light guide, a gas channel, and a second probe.

Optionally, the main connector comprises a second pad wherein, upon attachment of the main connector to said receptacle, the second probe abuts the second pad such that the second probe is compressed.

Optionally, the receptacle further comprises a second region and wherein said second region comprises a multi-pin interface configured to receive a second set of video data signals and wherein the second set of video data signals have a lower bandwidth than a bandwidth of the first set of video data signals.

Optionally, the first set of video data signals are generated by a CMOS sensor in the at least one viewing element and have a bandwidth greater than 1 GHz.

Optionally, the second set of video data signals are generated by a CCD sensor in the at least one viewing element and have a bandwidth less than 0.5 GHz.

Optionally, the first region comprises a light guide, a gas channel, a second probe, and a third probe, wherein the at least one probe, the second probe and third probe are positioned circumferentially around at least one of the light guide and gas channel and wherein each of the second probe and the third probe comprises a spring-loaded pin.

Optionally, the main connector comprises a second pad and a third pad and wherein, upon attachment of the main connector to said receptacle, the second probe abuts the second pad such that the second probe is compressed and the third probe abuts the third pad such that the third probe is compressed.

The present specification also discloses an endoscope system comprising: an endoscope comprising a tip section having a first viewing element and a second viewing element; a main connector coupled with the tip section and configured to receive and transmit a first set of video data signals from the first viewing element and a second set of video data signals from the second viewing element, wherein the main connector comprises a first pad in data communication with the first viewing element and a second pad in data communication with the second viewing element; and a control unit comprising a receptacle positioned on an exterior surface of the control unit and configured to receive the main connector, wherein the receptacle has a first region, wherein the first region comprises a first probe and a second probe, wherein each of the first probe and second probe comprises a spring loaded pin, and wherein, upon attachment of the main connector to said receptacle, the first probe abuts the first pad such that the first probe is compressed and the second probe abuts the second pad such that the second probe is compressed.

Optionally, each of the first pad and second pad is planar and metallic.

Optionally, the receptacle further comprises a second region wherein said second region comprises a multi-pin interface configured to receive a third set of video data signals and the third set of video data signals have a lower bandwidth than a bandwidth of the first set of video data signals or a bandwidth of the second set of video data signals.

Optionally, the first set of video data signals are generated by a CMOS sensor and have a bandwidth greater than 1 GHz.

Optionally, the third set of video data signals are generated by a CCD sensor and have a bandwidth less than 0.5 GHz.

The present specification also discloses an endoscope control unit configured to attach to, and be in data communication with, an endoscope, the endoscope control unit comprising a receptacle positioned on an exterior surface of the control unit and configured to receive a main connector of the endoscope; a first region positioned within an exterior face of the receptacle, wherein the first region comprises a first probe, wherein the first probe comprises a spring loaded pin configured to receive a first set of video data signals having a first bandwidth; a second region positioned within the exterior face of the receptacle and separated from the first region, wherein the second region comprises an interface configured to receive a second set of video data signals having a second bandwidth.

Optionally, the interface of the second region comprises a multi-pin interface configured attach to a complementary multi-pin interface in a connector of the endoscope.

Optionally, the first probe is configured to be compressed upon attachment of the receptacle to a connector of the endoscope.

Optionally, the first set of video data signals comprise digital data with a bandwidth greater than 1 GHz.

Optionally, the second set of video data signals comprise digital data with a bandwidth less than 0.5 GHz.

Optionally, the first region further comprises a light guide, a gas channel, a second probe, and a third probe, wherein the first probe, the second probe and third probe are positioned circumferentially around at least one of the light guide and gas channel and wherein each of the second probe and the third probe comprises a spring loaded pin.

The present specification also discloses an endoscope comprising: a tip section comprising a plurality of viewing elements coupled with at least one CMOS image sensor for transforming light captured by at least one viewing element into digital signals representing at least one image; and a main connector coupled with the tip section for transmitting the digital signals to a main control unit of the endoscope, the main connector comprising: a plurality of pads for transmitting the digital signals to a plurality of probes provided on a main connector housing of the main control unit, the probes comprising spring loaded tips pushing against the pads during the digital signal transmission.

Optionally, the viewing elements are cameras.

Optionally, the digital signal generated by the CMOS sensor is a high-speed signal having a bandwidth of 1.5 GHz.

Optionally, the number of pads provided on the main connector corresponds to the number of probes provided on the main connector housing.

Optionally, each pad is positioned on the main connector in alignment with a corresponding probe on the main connector housing of the main control unit.

The present specification also discloses a main connector of an endoscope coupled with a tip section comprising: a plurality of viewing elements coupled with at least one CMOS image sensor for transforming light captured by the viewing element into digital signals representing at least one image, wherein the main connector comprises a plurality of pads for transmitting the digital signals to a plurality of probes provided on a main connector housing of the main control unit, and wherein the probes comprise spring loaded tips pushing against the pads during the digital signal transmission.

The present specification also discloses a control unit for coupling with main connectors of endoscopes comprising one or both of CCD based sensors and CMOS based sensors for transforming light captured by one or more viewing elements of the endoscope into signals representing at least one image, the control unit comprising a plurality of probes for receiving the signals from the endoscope via a main connector comprising one or more pads for transmitting the signals, the probes comprising spring loaded tips pushing against the pads during the signal transmission.

The present specification also discloses an endoscope comprising: a tip section comprising a plurality of viewing elements coupled with at least one or both of a CMOS image sensor and a CCD image sensor for transforming light captured by the viewing element into digital and/or analog signals; and a main connector coupled with the tip section for transmitting the signals to a main control unit of the endoscope, wherein the main connector comprises: a plurality of pads for transmitting digital signals provided by the CMOS image sensor to a plurality of probes provided on a main connector housing of the main control unit; and a connector for transmitting the analog signals having a bandwidth of less than 0.5 GHz provided by the at least one image sensor via the main connector housing of the main control unit.

Optionally, the viewing elements are cameras.

Optionally, the digital signal generated by the CMOS sensor is a high-speed signal having a bandwidth of 1.5 GHz.

Optionally, the main connector comprises a plurality of pads for transmitting the digital signals to a plurality of probes provided on a main connector housing of the main control unit, the probes comprising spring-loaded tips pushing against the pads during the digital signal transmission.

Optionally, the main connector comprises a plurality of pads for transmitting the digital signals to a plurality of twisted pair cables provided on a main connector housing of the main control unit.

Optionally, the number of pads provided on the main connector corresponds to the number of probes provided on the main connector housing.

Optionally, each pad is positioned on the main connector in alignment with a corresponding probe on the main connector housing of the main control unit.

The present specification also discloses an endoscope comprising: a tip section comprising a plurality of viewing elements coupled with at least one image sensor for transforming light captured by the viewing elements into signals, and a main connector coupled with the tip section for transmitting the signals to a main control unit of the endoscope; the main connector comprising: a LEMO® connector for transmitting analog signals provided by the at least one image sensor via the main connector housing of the main control unit, and at least one pad for transmitting digital signals provided by at least one image sensor to at least one probe provided on a main connector housing of the main control unit.

Optionally, the at least one image sensor is a CMOS sensor. Still optionally, the at least one image sensor is a CCD sensor.

Optionally, the at least one probe is adapted to connect with at least one connection means for transmitting digital signals provided by the CMOS image sensor. Still optionally, the connection means may be one of a spring loaded push-pin probe, coaxial probe or twisted pair.

The present specification also disclose an endoscope comprising: a tip section comprising at least one viewing element coupled with an image sensor for transforming light captured by the at least one viewing element into signals, and a main connector coupled with the tip section for transmitting the signals to a main control unit of the endoscope, wherein the main connector comprises: a LEMO® connector for transmitting the analog signals provided by the image sensor via the main connector housing of the main control unit, and at least one pad for transmitting digital signals provided by the image sensor to at least one probe provided on a main connector housing of the main control unit.

Optionally, the at least one image sensor is a CMOS sensor. Still optionally, the at least one image sensor is a CCD sensor.

Optionally, the at least one probe is adapted to connect with at least one connection means for transmitting digital signals provided by the CMOS image sensor. Still optionally, the connection means may be one of a spring loaded push-pin probe, coaxial probe or twisted pair.

The present specification also discloses a control unit for coupling with main connectors of endoscopes comprising one or both of CCD based sensors and CMOS based sensors for transforming light captured by one or more viewing elements of the endoscope into digital and/or analog signals representing at least one image, the control unit comprising a plurality of probes for receiving the digital and/or analog signals from the endoscope via a main connector comprising one or more pads for transmitting the digital and/or analog signals, the probes comprising spring loaded tips pushing against the pads during the digital and/or analog signal transmission.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 5A illustrates a main connector housing/receptacle of a main control unit that is interchangeably compatible with both a CCD-based endoscope as well as a CMOS-based endoscope, in accordance with an embodiment of the present specification;

FIG. 5B illustrates a main connector housing/receptacle of a main control unit that is interchangeably compatible with both a CCD-based endoscope as well as a CMOS-based endoscope, in accordance with an embodiment of the present specification;

FIG. 5C is a diagram of a probe employed in a main connector housing, in accordance with an embodiment of the present specification;

FIG. 6A is an illustration of a main connector of an endoscope comprising CMOS sensors, in accordance with an embodiment of the present specification;

FIG. 6B is an illustration of a main connector of an endoscope comprising CMOS sensors, in accordance with an embodiment of the present specification;

DETAILED DESCRIPTION

Figure 1A:
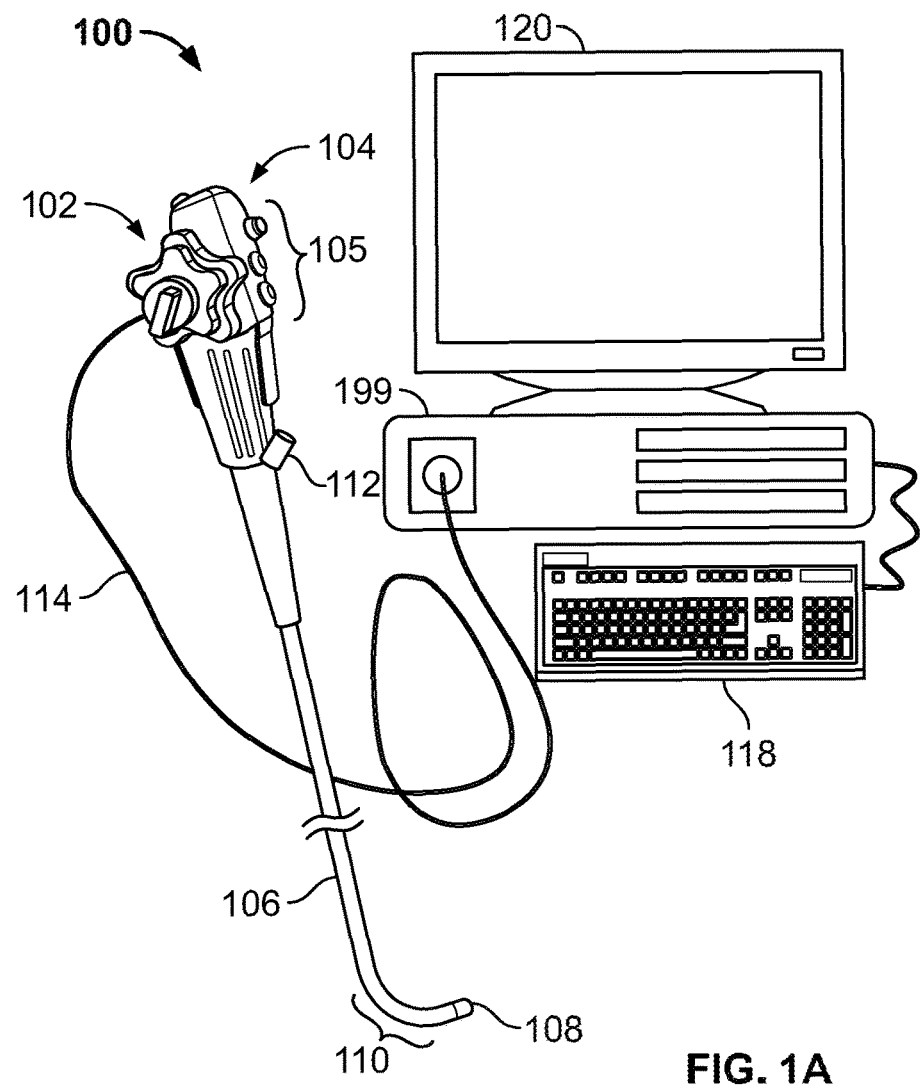
FIG. 1A shows a semi-pictorial view of a multi-camera endoscopy system, according to some embodiments.

The present specification provides an endoscope that uses CMOS sensors in conjunction with cameras for capturing images of internal organs and converting the same into digital data. In an embodiment, the present specification provides a main control unit comprising an electrical interface for recognizing and subsequently connecting with both a CMOS sensor-based endoscope as well as a CCD sensor-based endoscope. In an embodiment, the present specification provides a main connector for CMOS based endoscopes comprising connector pads for connecting with probes provided on a main control unit of the endoscope. In some embodiments, the probe is a spring-loaded push-pin probe.

In some embodiments, the present specification describes a main connector that can securely connect with a high-speed transmission interface provided in the main control unit. It should be appreciated that the term "pads" or "plurality of pads" refers to one or more planar surfaces, preferably metallic, configured to interface with the probes described herein. It should further be appreciated that the planar pad surface, with or without any extensions or members around a periphery of the pad, is configured to compress the probe, to thereby establish a data connection.

It is noted that the term "endoscope" as mentioned herein may refer particularly to a colonoscope, according to some embodiments, but is not limited only to colonoscopes. The term "endoscope" may refer to any instrument used to examine the interior of a hollow organ or cavity of the body.

It should also be noted that a plurality of terms, as follows, appearing in this specification are used interchangeably to apply or refer to similar components and should in no way be construed as limiting:

"Utility tube/cable" may also be referred to as an "umbilical tube/cable".

A "main control unit" may also be referred to as a "controller unit", "main controller" or "fuse box".

A "viewing element" may also be referred to as an image capturing device/component, viewing components, camera, TV camera or video camera.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. In addition, the terminology and phraseology is used for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Reference is now made to FIG. 1A, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108, which is turnable by way of a bending section 110. Handle 104 may be used for maneuvering elongated shaft 106 within a body cavity. The handle may include one or more buttons and/or knobs and/or switches 105, which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. In embodiments, utility cable 114 connects with the main control unit 199 via a main connector (shown in FIG. 2A). Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images and/or video streams of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s), which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1A, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the images and/or video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these images and/or video streams may be processed by the main control unit 116 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. patent application Ser. No. 14/263,896, entitled "Video Processing in A Compact Multi-Viewing Element Endoscope System", and filed on Apr. 28, 2014, which is herein incorporated by reference in its entirety.

Figure 1B:
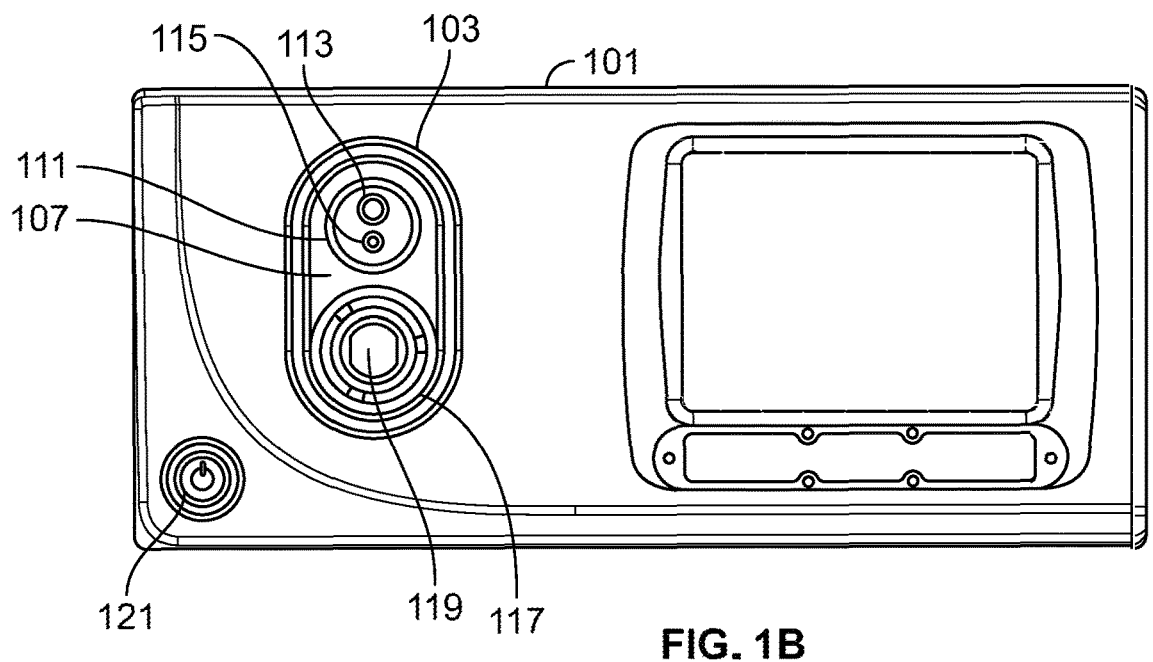
FIG. 1B shows a perspective view of one embodiment of a front panel of a main control unit of a multi-camera endoscopy system.

FIG. 1B shows a perspective view of one embodiment of a control panel of a main control unit of a multi-camera endoscopy system. As shown in FIG. 1B, the control panel 101 contains a main connector housing 103 having a front panel 107. The main connector housing front panel 107 comprises a first section 111, containing a light guide opening 113 and a gas channel opening 115, and a second section 117, comprising a utility cable opening 119. The light guide opening 113 and gas channel opening 115 are configured to receive and connect with a light guide and a gas channel respectively, on a main connector, and the utility cable opening 119 is configured to receive and connect with an electric connector of a scope. A switch 121 is used to switch on and switch off the main control unit.

Figure 2A:
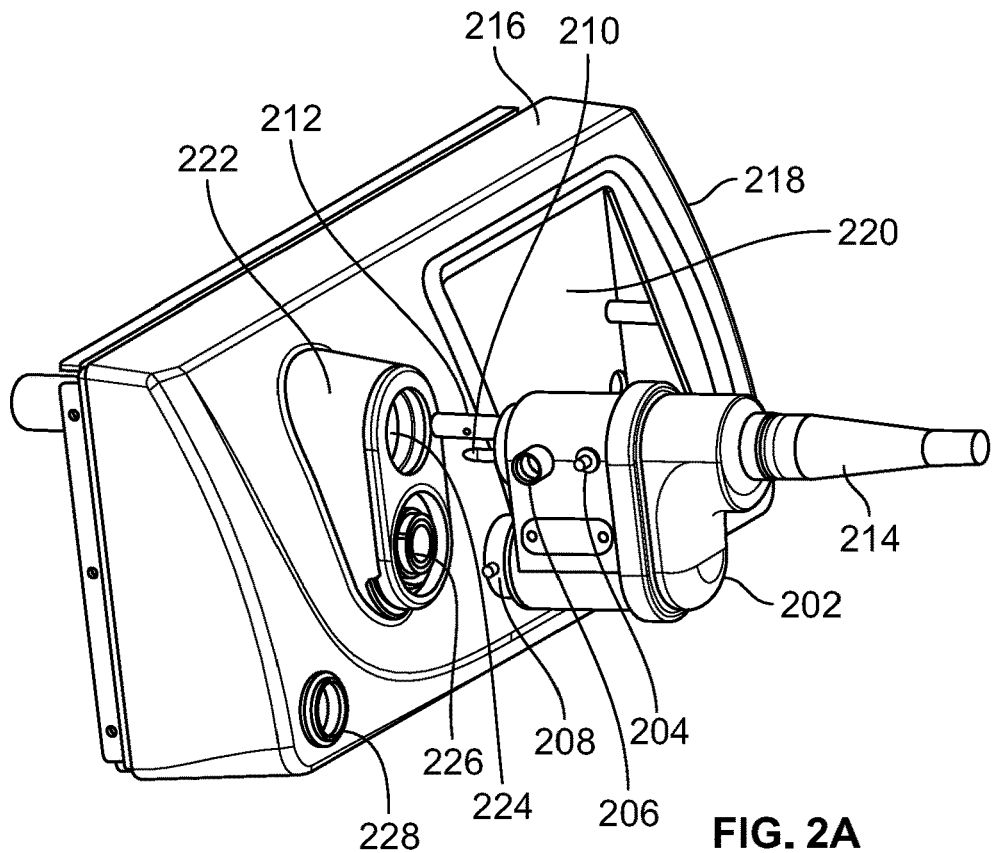
FIG. 2A illustrates a system for connecting a main connector to a main control unit of an endoscope, in accordance with an embodiment of the present specification.

FIG. 2A illustrates a main connector proximate to a main control unit, in accordance with an embodiment of the present invention. As illustrated, the main connector 202 comprises a jet connector 204, wherein the jet connector 204 is typically connected to a fluid supplier to provide fluid to a jet opening in an endoscope tip, a water bottle connector 206, wherein the water bottle connector 206 is typically engaged to a water supplier, such as a water bottle or hospital facilities, to provide fluid to an insufflation and/or irrigation system placed within the endoscope tip, an electric connector 208, wherein the electric connector 208 connects between electronics components within the endoscope, such as but not limited to, sensors, illuminators, handle of the endoscope and the main control unit to provide electricity to the various components, a gas channel 210, wherein the gas channel 210 typically provides gas flow to the tip of the endoscope and a light guide pin 212. The main connector 202 is connected with a utility cable 214. The main control unit 216 comprises a front panel 218 having a screen 220 for operation information concerning an endoscopy procedure when the endoscope is in use. The main control unit 216 also comprises a main connector housing 222 for receiving the main connector 202. The main connector housing 222 comprises a first section 224 for connecting with the light guide pin 212 and the gas channel 210 and a second section 226 for receiving the electric connector 208. The front panel 218 further comprises a button 228 for switching the main control unit 216 on or off.

Figure 2B:
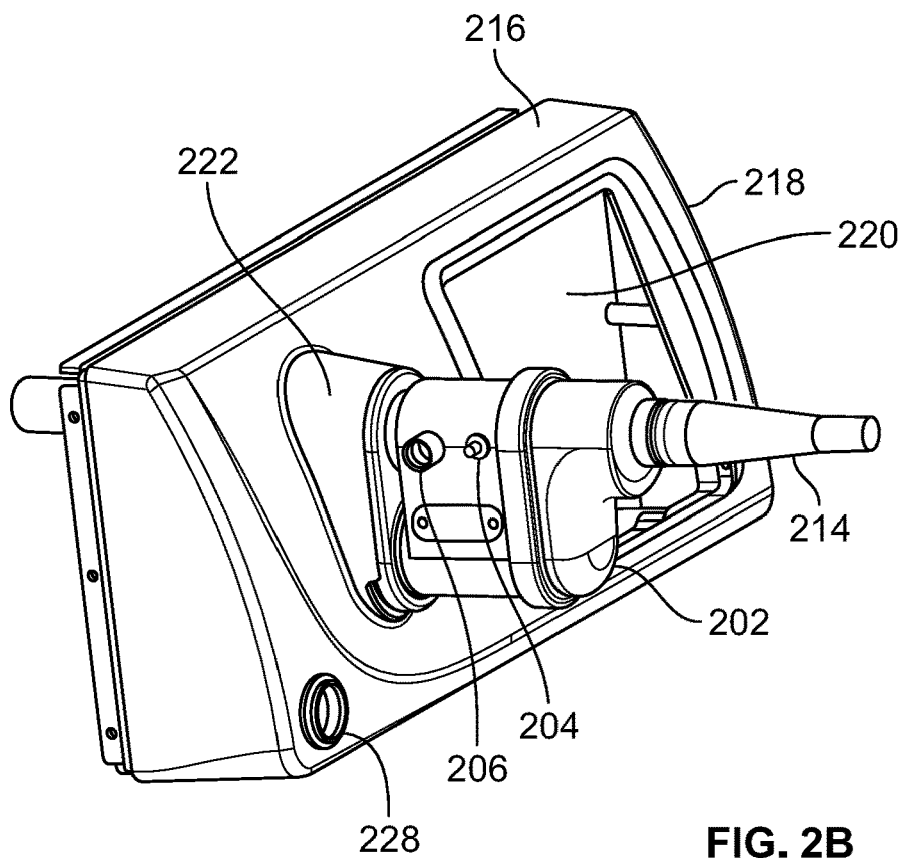
FIG. 2B illustrates a main connector securely connected to a main control unit, in accordance with an embodiment of the present specification.

FIG. 2B illustrates a main connector securely connected to a main control unit, in accordance with an embodiment of the present invention. Referring to both FIGS. 2A and 2B, in various embodiments, the main connector 202 is connected to the main control unit 216 when the light guide pin 212 and the gas channel 210 are inserted into a light guide opening and a gas channel opening, respectively both placed within the first section 224 opening of the main connector housing 222. Also, electric connector 208 is inserted into the second section 226 opening of the main connector housing 222.

Figure 3:
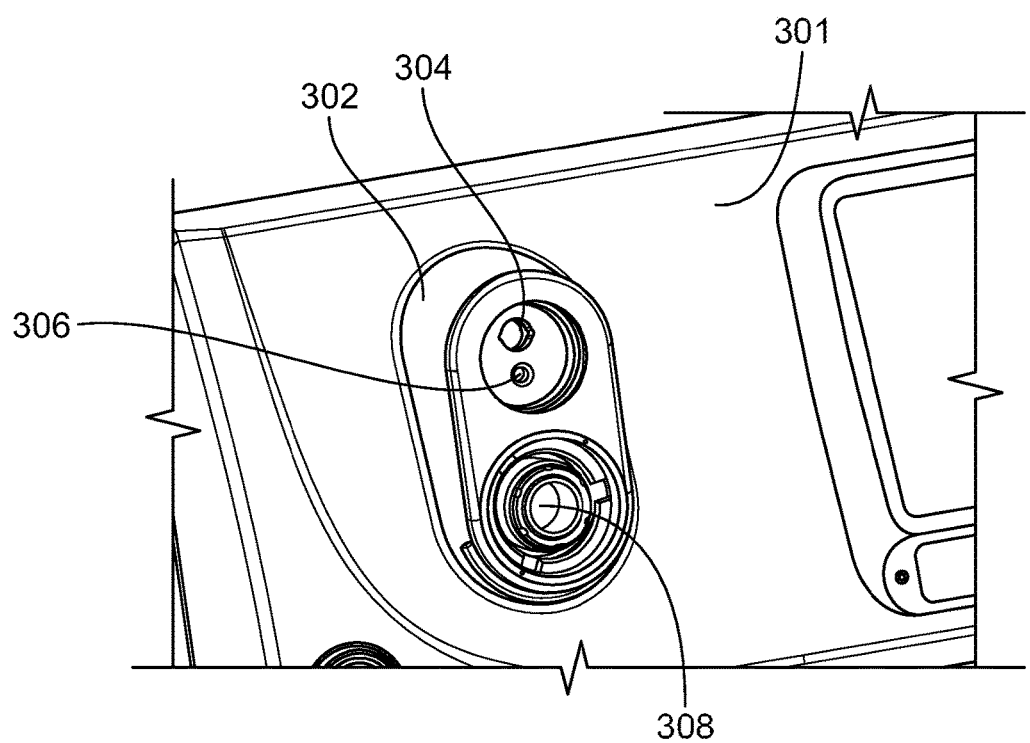
FIG. 3 illustrates a main connector housing on a front panel of a main control unit of an endoscope.
Figure 4:
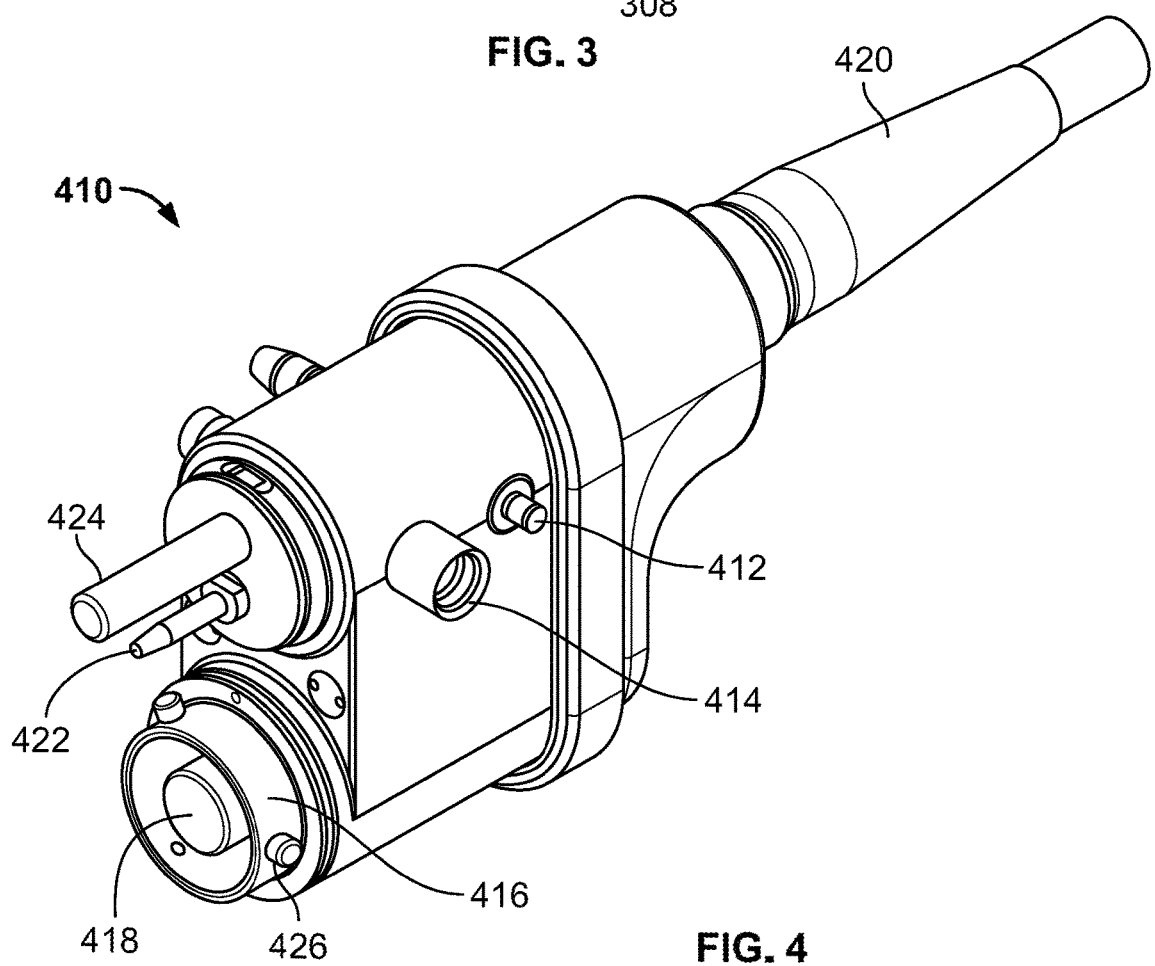
FIG. 4 illustrates a main connector of the endoscope.

FIG. 3 illustrates a main connector housing/receptacle on the main control unit front panel of an endoscope. FIG. 4 illustrates a main connector of an endoscope. Referring to FIGS. 3 and 4 simultaneously, the main control unit front panel 301 comprises a receptacle 302 comprising two sections, a first section comprising a light guide opening 304 and a gas channel opening 306 and a second section comprising a utility cable opening 308. The gas channel opening 306 receives and connects with a gas channel (shown in FIG. 2A) and the utility cable opening 308 receives and connects with a main connector (shown in FIG. 2A). In embodiments, the utility cable opening 308 comprises a push/pull electric connector interface, such as a LEMO® connector interface, which is commonly known in the art. Endoscopes comprising viewing elements coupled with CCD sensors are equipped with LEMO® connectors for transmission of the analog image signals captured by the viewing elements and CCD sensors to the main control unit via the utility cable opening 308 having the LEMO® connector interface.

However, endoscopes comprising CMOS sensors coupled with viewing elements for capturing images and videos of internal body organs that are being endoscopically scanned require a separate connection interface for transmission of the captured digital signals as these signals cannot be transmitted via a LEMO® interface. In an embodiment, an interface (described with reference to FIG. 5A), comprising probes used for transmitting such signals, may optionally also be provided on the receptacle 302 and is described with reference to FIG. 5A. The receptacle 302 may also comprise locking elements such as but not limited to a mechanical lever adjusted to mechanically engage and disengage the main connector from receptacle 302.

As illustrated in FIG. 4, the main connector 410 comprises a jet connector 412, a water bottle connector 414, and an electrical connector 416. Referring to FIGS. 3 and 4 simultaneously, in an embodiment, electrical connector 416 comprises, but is not limited to, a LEMO® connector 418, which connects with a LEMO® connector interface in the utility cable opening 308 provided on receptacle 302 of front panel 301 of the main control unit of the endoscope. It should be noted herein, as described in further detail below, that electrical connector 416 may also comprise a connector interface that enables connection of a CMOS-image based endoscopic device. Electrical connector 416 connects the electronics components within the endoscope, such as but not limited to, sensors, illuminators, handle of the endoscope to the main control unit via a utility cable 420. Utility cable 420 may include therein one or more fluid channels and one or more electrical channels. The electrical channel(s) may include at least one data cable for receiving video signals from the front and at least one side-pointing viewing elements, as well as at least one power cable for providing electrical power to the viewing elements and to the discrete illuminators. In endoscopes comprising CCD sensors coupled with the viewing elements, the data cable transmits the analog image signals captured by the viewing elements to the main control unit via LEMO® connector 418, which connects with the LEMO® connector interface 308 provided on receptacle 302 of the main control unit. In various embodiments, the data cable of the utility cable 420 also transmits digital signals provided by CMOS sensors present in the endoscope's tip to the main connector and then to the main control unit via connection means such as those described in FIGS. 5A, 5B and 5C provided on the main connector and the receptacle of the main control unit.

Main connector 410 further comprises a gas channel 422, which connects with the gas channel opening 306 and a light guide pin 424, which goes into the light guide opening 304 of receptacle 302 in order to connect the main connector 410 with the main control unit. Main connector further comprises pins 426, which enable secure locking of the main connector 410 with the utility cable opening 308. Also in embodiments, a connector cover cup may be provided to cover the electrical connector 416 during reprocessing cycles (washing/cleaning) of the endoscope in order to make the endoscope waterproof.

FIG. 5A illustrates a main connector housing of a main control unit that is compatible with both a CCD-based endoscope as well as a CMOS-based endoscope, in accordance with an embodiment of the present specification. Receptacle 500 is provided on a main control unit of an endoscope system as illustrated in FIGS. 1B, 2A, 2B and 3. The receptacle 500 comprises a first section 502 and a second section 510. In various embodiments, the second section 510 comprises a multi-pin analog interface 512 (308 of FIG. 3), such as a LEMO® interface, that is used to transmit analog signals captured by CCD sensors coupled with viewing elements of the endoscope to the main control unit. The first section 502 comprises openings 504 and 506 for connecting with a light guide pin and a gas channel, respectively, of a main connector of an endoscope. Further, since receptacle 500 is compatible with an endoscope having CMOS sensors coupled with viewing elements/cameras, the first section 502 also comprises at least one probe 508, which is used to transfer the high frequency digital image and video signals captured by the CMOS sensors and viewing elements to the main control unit. In embodiments, the at least one probe is preferably a spring-loaded push pin probe.

More generally, the main connector housing 500, which is configured to receive a proximal end of an endoscope, comprises two distinct connection regions that are separated by a planar portion of the housing 500. The first connection region comprises receiving portions 504 and 506 for connecting with a light guide pin and a gas channel, respectively, of a main connector of an endoscope. Positioned circumferentially around the light guide pin and gas channel are one or more interfaces 508 configured to receive digital data having a bandwidth of 1 GHz or more from one or more complementary interfaces positioned in the main connector of an endoscope. In an embodiment, an exemplary interface comprises a coaxial probe interface having a spring-loaded signal pin that compresses upon coupling with a complementary pad in the endoscope main connector and is adapted to receive digital transmissions having bandwidths of more than 1 GHz. In an embodiment, an exemplary interface comprises a probe interface having a spring-loaded pushpin. In another embodiment, an exemplary interface comprises a coaxial female receiver that receives a complementary male coaxial single pin connector and is optimized to receive digital signals having greater bandwidth than the data transmissions in the second region. The probe compression and pad combination is preferred, however, because it obviates the need for a user to precisely align multiple extending members with multiple holes in order to achieve the requisite fit. Rather, using compressible pins and pads, the digital data connections in the first region are automatically achieved when the other components, such as the light guide, gas channel, and second region analog connections, are properly mated.

The second connection region comprises a receiver interface that is adapted to connect to, and receive data through, one or more multi-pin analog connectors. An exemplary interface comprises a multi-pin interface that receives a single coaxial, push-pull, multi-pin connector and is adapted to receive analog transmissions having bandwidths of less than 0.5 GHz. In another embodiment, an exemplary interface comprises a multi-pin interface that receives a single coaxial, push-pull, multi-pin connector and is optimized to receive analog signals having less bandwidth than the data transmissions in the first region.

It should be appreciated that the light guide pin and gas channel could be positioned in the second region, rather than the first, that the light guide pin could be positioned in the second region while the gas channel is in the first region, or that the light guide pin could be positioned in the first region while the gas channel is in the second region. It should further be appreciated that the positions of the planar pad structures in the endoscope connector, configured to mate with the spring-loaded pin probes in the first region of the receptacle, can be switched, thereby placing the planar pad structures in the receptacle and the spring loaded pins in the endoscope connector.

In an embodiment, first section 502 comprises at least two probes 508 (one for each viewing element/camera of the endoscope) for transferring high-speed image and video data captured by using CMOS sensors from the endoscope to the main control unit via the receptacle 500. In an embodiment, first section 502 comprises at least three probes 508 (one for each viewing element/camera of the endoscope) for transferring high-speed image and video data captured by using CMOS sensors from the endoscope to the main control unit via the receptacle 500. In various embodiments, the probes 508 may be placed at any location on the receptacle 500.

FIG. 5B illustrates another exemplary position of the probes 508 shown in FIG. 5A, in accordance with an embodiment of the present specification. As shown in FIG. 5B the probes 508 are positioned in the second section 510, which also comprises the electrical push/pull multi-pin interface 512 for connecting with a main connector of a CCD based endoscope. The probes 508 transfer high-speed image and video data, captured using CMOS sensors, from the endoscope to the main control unit via the receptacle 500.

In an embodiment, a probe 508 has an impedance of 50 ohms, is capable of transmitting high-speed signals in the range of 0 to 2 GHz capacity without compromising the signal integrity, and comprises a spring-loaded tip. In embodiments, any commonly available probe capable of transmitting high-speed signals of about 2 GHz may be employed in the main connector housing/receptacle 500. In an embodiment, probes designed to make a spring-loaded connection to sub miniature version A (SMA) sockets may be employed, as this substitutes the need for sacrificial plugs and sockets. In an exemplary embodiment, a probe having the following specifications may be employed:

Impedance: 50 Ohms;
Working travel: 4.24 mm (0.167");
Spring force at working travel for outer shield: 57 g (2.0 oz);
Spring force at working travel for inner contact: 113 g (4.0 oz);
Current rating (DC): 3 Amp;
Maximum Frequency (3 db c/o): 2.5 GHz;
YSWR: 1.15:1@1 GHz;
Ins loss: 0.13 db@1 Ghz;
Required tail connector: SMB Plug.

FIG. 5C illustrates a diagrammatical view of a probe employed in a main connector housing, in accordance with an embodiment of the present specification. Probe 508 comprises a spring loaded tip portion 514 and an insulator portion 516 surrounded by a metallic shield 518. Probe 508 transfers high speed digital image and video signals captured by CMOS sensors provided in an endoscope's tip portion via a utility cable to a main connector of the endoscope and then to the endoscope's main control unit via SMA connectors provided within the receptacle 500 into which a distal end 520 of the probe 508 is fitted. In various embodiments, the same utility cable that is used to transfer images captured by the CCD sensors of the endoscope to the control unit is used for transferring high-speed digital image and video signals captured by CMOS sensors provided in an endoscope's tip to the control unit.

FIGS. 6A and 6B illustrate a main connector of an endoscope comprising CMOS sensors, in accordance with an embodiment of the present specification. As illustrated in FIG. 6A, main connector 600 comprises a first section 602 which further comprises at least a light guide pin 604, which fits into a light guide pin opening (such as opening 504 shown in FIG. 5A) on a main control unit; and a gas channel 606, which fits into a gas channel opening (such as opening 506 shown in FIG. 5A) on a main control unit. First section 602 is also equipped with one or more pads 608, such that each pad is placed in alignment with a probe (such as probe 508 shown in FIG. 5A) provided on a receptacle of a main control unit of the endoscope. Main connector 600 may also comprise a second section 612, which includes a LEMO® connector 610.

FIG. 6B illustrates a main connector 600 comprising a first section 602 which further comprises at least a light guide pin 604, which fits into a light guide pin opening (such as opening 504 shown in FIG. 5B) on a main control unit; and a gas channel 606 which fits into a gas channel opening (such as opening 506 shown in FIG. 5B) on a main control unit. A second section 612 of main connector 600 comprises the LEMO® connector 610 and is also provided with one or more pads 608, such that each pad is placed in alignment with a probe (such as probe 508 shown in FIG. 5B) provided on a receptacle of a main control unit of the endoscope. Pads 608 are resistant to aggressive substances. Between each medical procedure, the endoscope must be reprocessed, which may include the use of chemical ingredients to clean the endoscope and prepare it for the next patient. In various embodiments, pads 608 are resistant towards alteration or damage by any chemicals used for reprocessing the endoscope. In various embodiments, the pads 608 are commonly available and comprise a metal coating/cover for establishing an electrical connection with tips of cables, such as but not limited to coaxial cables. In an embodiment, pads 608 are covered with gold for enabling connectivity.

When the connector 600 is connected to a main control unit's receptacle, such as shown in FIGS. 5A, 5B, the pads 608 press against spring loaded tips of the probes causing a secure connection through which high-speed signals from CMOS sensors employed in the endoscope's tip may be transmitted to the main control unit. The high speed signals are transferred from the viewing elements to the pads 608 via the utility cable (shown in FIG. 1A); and from the pads 608 to the main control unit via the cables through the probes provided on the receptacle.

In various embodiments, the number of pads 608 provided on main connector 600 corresponds to the number of probes provided on the main control unit. In the embodiment illustrated in FIGS. 5A, 5B and 6A, 6B, each probe and pad pair is coupled with a viewing element placed in a tip portion of the endoscope for transmitting the image/video captured by the viewing element to the main control unit. Main connectors of endoscopes employing only CCD based image sensors are not provided with pads 608. Image data from such endoscopes is transmitted to the main control unit via LEMO® connector 610 provided on the second section 612 of main connector 600. In an embodiment, pads 608 may be replaced by any other suitable connecting element for transferring high-speed signals from CMOS sensors employed in the endoscope's tip to the main control unit via the main connector.

In another embodiment, twisted-pair cabling commonly known in the art may be used for transferring the high frequency digital image and video signals captured by the CMOS sensors and viewing elements to the main control unit, instead of coaxial cables. Twisted pair cabling is a type of wiring in which two conductors of a single circuit are twisted together for the purposes of canceling out electromagnetic (EMI) from external sources. Referring to FIGS. 5A and 5B, in an embodiment, first section 502 comprises at least one twisted pair for transferring high-speed video data from the endoscope to the main control unit via the receptacle 500.

As may be apparent to persons of skill in the art, in various embodiments, other suitable means may be provided on the endoscope connector and receptacle, to transfer high speed video data from CMOS sensors of the endoscope to the main control unit, along with a LEMO® connector; thereby making the endoscope and receptacle compatible with both CCD and CMOS sensors.

Figure 7:
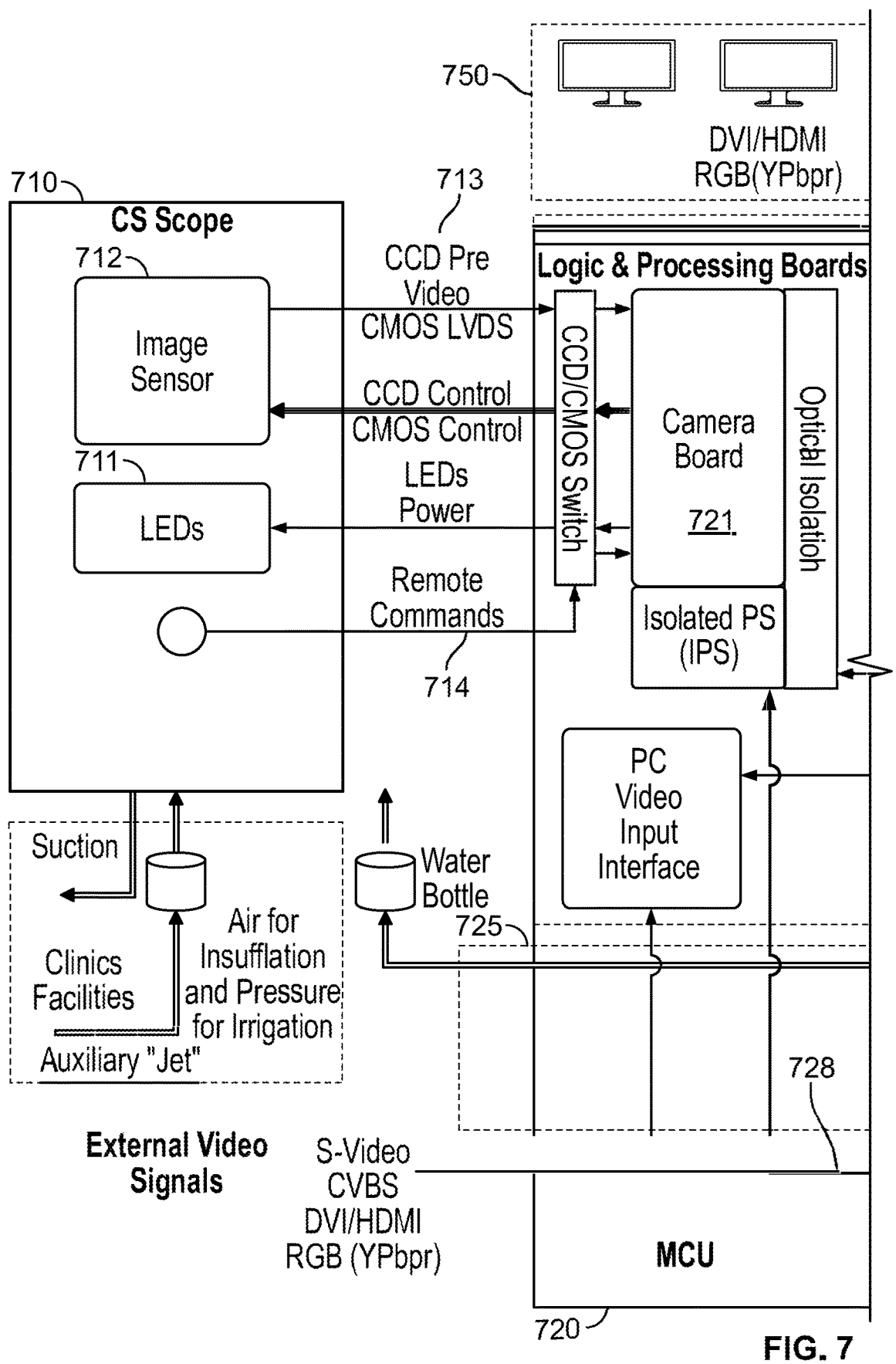
FIG. 7 details how a video controller or the controller circuit board of the main controller of an endoscope operatively connects with the endoscope and its display units.
Figure 7:
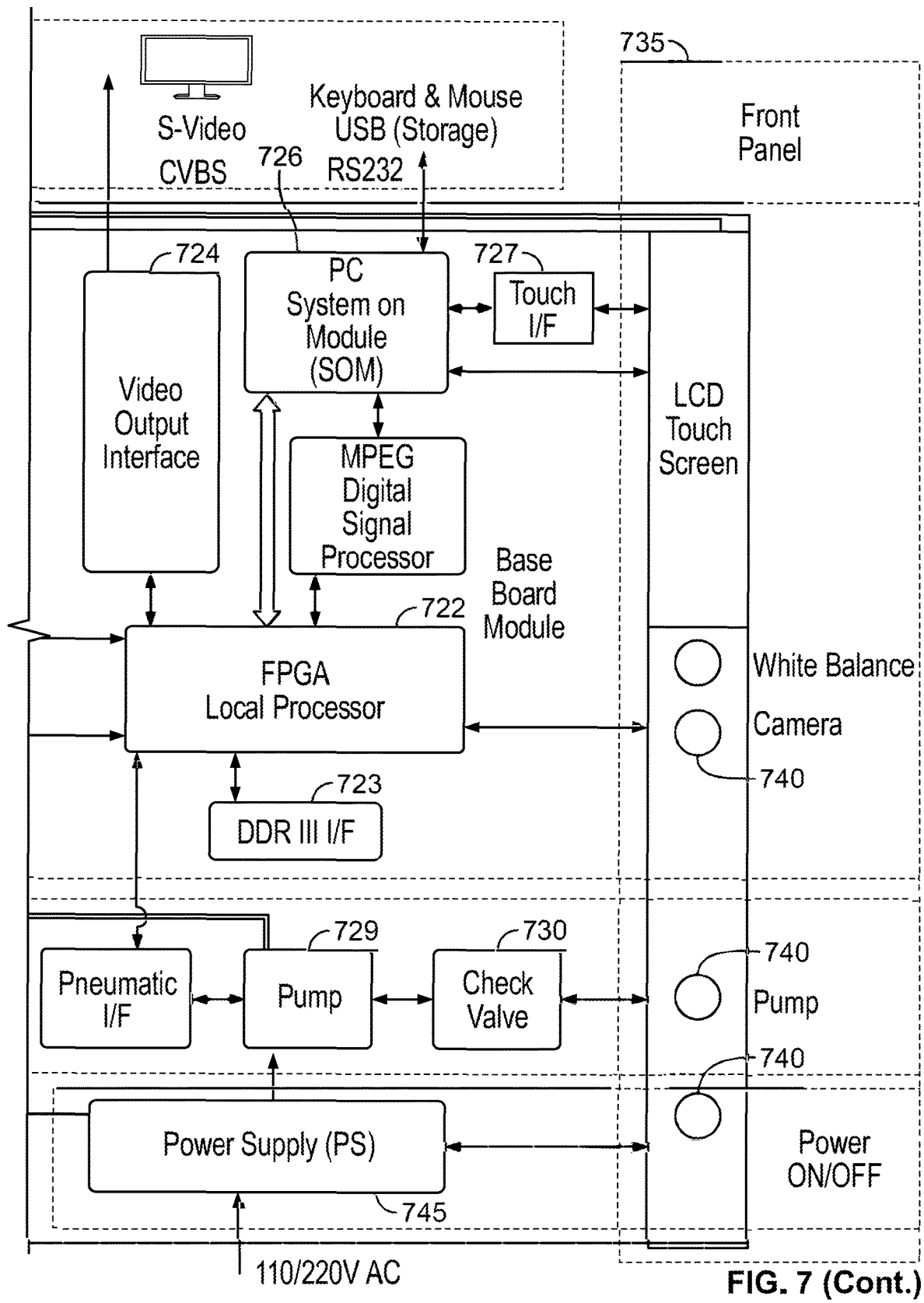

FIG. 7 details how a video controller or the controller circuit board 720 of the main controller of an endoscope operatively connects with the endoscope 710 and the display units 750. Referring to FIG. 7, video controller/controller circuit board 720 comprises a camera board 721 that controls the power supplies to the LEDs 711, transmits controls for the operation of image sensor(s) 712 (comprising one or more cameras) in the endoscope, and converts pre-video signals from image sensors to standard video signals. The image sensor 712 may be a charge coupled device (CCD) or a complementary metal oxide semiconductor (CMOS) imager. The camera board 721 receives pre-video signal(s) 713 generated by the CCD imager and also other remote commands 714 from the endoscope 710.

Controller circuit board 720 further comprises elements for processing the video obtained from the image sensors 712 through the camera board 721, as well as other elements for system monitoring and control.

These elements are connected with the Base Board Module 752, which is a PCB. In one embodiment, elements which are ICs (Integrated Circuits) are connected by soldering, element 726 (SOM or System on Module) is connected by mounting, while all other elements are connected by means of cables.

Various elements on the Base Board Module 9052 are described as follows:

FPGA (Field Programmable Gate Array) 723:

FPGA 723 is a logic device programmed specifically for the system requirements and performs tasks that may be categorized by two types: logic tasks which are preferably implemented by hardware (as opposed to software), and logic tasks related to video image processing. In one embodiment, the Base Board Module 752 includes one or more double data rate type three synchronous dynamic random access memory modules (DDR3) 733 in communication with the FPGA 723.

Logic tasks, which are preferably implemented by hardware, include, but are not limited to:
  Initializing some Base Board Module's 752 ICs upon system power-up;
  Monitoring the buttons 740 for White Balance, LED on/off, Air Flow, and Power on/off on the front-panel 735;
  Monitoring SOM's 726 proper operation using a watchdog mechanism;
  Backing-up some of the system's parameters (example: airflow level), even while the system is switched off; and
  Communicating with the Camera Board 721.

Logic tasks related to video image processing, which are implemented by software or hardware include, but are not limited to:
  Multiplexing video inputs—Each of the multiple imaging elements has several video interfaces, which are multiplexed via Video Input Interface 751. Further, several auxiliaries are multiplexed via Auxiliary Video Input Interface 725.
  Optional digital signal processor (DSP) 722 playback output and DSP record input.
  Internal test pattern to video outputs via Video Output Interface 724 to multiple displays.
  Conversion between cameras' video standard to display video standard.
  OSD (On Screen Display) insertion, also known as graphic overlay.
  PIP (Picture-in-Picture).

Stitching images from several cameras into one image displayed on a single screen.

Image adjustments, such as brightness, contrast, etc.

DSP (Digital Signal Processor) 722:

DSP 722 is used for recording compressed (coded) video and playing back decompressed (decoded) video. In one embodiment, the standard of compressed video is H264 or equivalent (such as MPEG).

Operationally, FPGA 723 selects for the DSP 722 the desired video to be recorded, i.e. any of the inputs, or, more likely, a copy of one or more of the screens. In the latter case, this includes the OSD and format conversion. In the likely case of the screen's format differing from that of DSP's 722 required video input format, the FPGA 723 also converts the screen's format to the desired DSP 722 format while transmitting video to the DSP 722.

Auxiliary Video Input Interface 725:

In one embodiment, the video input to the Auxiliary Video Input Interface 725 may comprise analog video, such as in CVBS (color, video, blanking, sync), S-Video or YPBPR format or digital video (DVI), and may be displayed as such.

SOM (System on Module) 726:

The SOM 726 provides an interface to input devices such as keyboard, mouse, and touchscreen via Touch I/F 727. Through these input devices, together with the buttons 740 in the Front Panel 735, the user controls the system's functionality and operational parameters. In one embodiment, a peripheral component interconnect express (PCIe) bus connects the SOM 726 with the FPGA 723. Most common types of data traffic over the PCIe are:

a. SOM 726 to FPGA 723: Commands (for example, when the user changes operational parameters); and b. FPGA 723 to SOM 726: Registers values, which provide an indication of the internal status, and captured images.

Other Functionalities:

The controller circuit board 720 may further control one or more fluid, liquid and/or suction pump(s), which supply corresponding functionalities to the endoscope through pneumatic I/F 728, pump 729 and check valve 730. The controller circuit board 720 further comprises an on-board power supply 745 and a front panel 735, which provides operational buttons 740 for the user.

The camera board 721 receives video signal 713 which, in one embodiment, comprises three video feeds, corresponding to video pickups by three endoscopic tip viewing elements (one front and two side-looking viewing elements), as generated by the image sensor 712. In one embodiment, the three video feed pickups, corresponding to the three viewing elements (the front-looking, left-side looking and right-side looking viewing elements) of an endoscopic tip, are displayed on three respective monitors.

Figure 8:
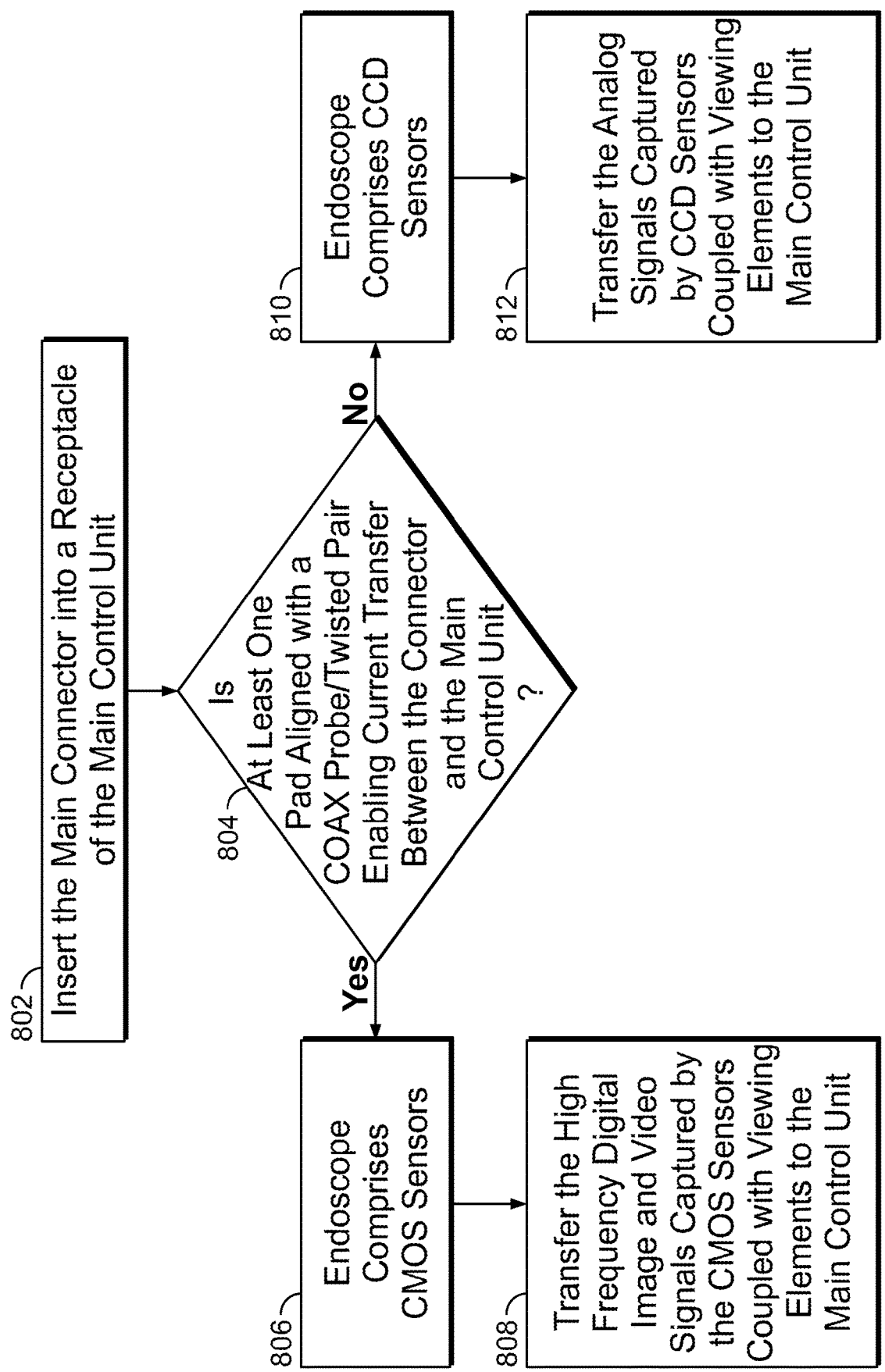
FIG. 8 is a flowchart illustrating a method of detecting and transferring signals captured by using CCD or CMOS sensors coupled with viewing elements of an endoscope, from the endoscope to a main control unit, in accordance with an embodiment of the present specification.

FIG. 8 is a flowchart illustrating the method of detecting and transferring signals captured by using CCD or CMOS sensors coupled with viewing elements of an endoscope, from the endoscope to a main control unit, in accordance with an embodiment of the present specification. In various embodiments, the endoscope is provided with means to transfer both the analog signals captured by using CCD sensors as well as high speed digital signals captured by using CMOS sensors and the main control unit is provided with means for receiving both the kinds of signals. In embodiments, the endoscope is connected to the main control unit by using a connector comprising a LEMO® connector (such as LEMO® connector 610 shown in FIGS. 6a-6B) as well as one or more pads (such as pads 608 shown in FIGS. 6A-6B); and the main control unit comprises a receptacle having both a LEMO® interface (such as LEMO® interface 512 shown in FIGS. 5A-5B) and at least one probe (such as probe 508 shown in FIGS. 5A-5B) or a twisted pair cable.

At step 802, the main connector of the endoscope is inserted into the receptacle of the main control unit for transferring the signals captured by the viewing elements of the endoscope coupled with either CMOS or CCD sensors, to the main control unit. At step 804, it is determined if at least one pad of the connector is aligned with either a probe, such as a spring-loaded push-pin probe or a twisted pair cable present on the receptacle of the main controller. If at least one pad of the connector is aligned with either a probe or a twisted pair cable present on the receptacle, then at step 806 it is determined that the endoscope comprises CMOS sensors. Next, at step 808, high-speed image and video digital signals captured by using CMOS sensors coupled with the viewing elements of the endoscope are transferred to the main control unit via the connection between the pads on the connector and the probes or the twisted pair cables on the receptacle. If at least one pad of the connector is not aligned with either a probe or a twisted pair cable present on the receptacle, then at step 810 it is determined that the endoscope comprises CCD sensors. Next, at step 812 analog signals captured by using CCD sensors coupled with the viewing elements of the endoscope are transferred to the main control unit via the connection between the LEMO® connector provided on the endoscope's connector and the LEMO® interface provided on the receptacle.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A medical device comprising:
a cable extending longitudinally from a distal end to a proximal end;
an image sensor; and
a connector at the proximal end of the cable, the connector comprising:
a first region, wherein the first region comprises a first interface configured to transmit a first set of video data signals having a first bandwidth of more than 1 GHz; and
a second region spaced from the first region, wherein the second region comprises a second interface configured to transmit a second set of video data signals having a second bandwidth.

2. The medical device of claim 1, wherein the second bandwidth is less than 0.5 GHz.

3. The medical device of claim 1, wherein the first interface is at least one pad.

4. The medical device of claim 3, wherein the at least one pad is configured to (i) abut at least one probe of a receptacle and (ii) transmit the first set of video data signals to the at least one probe.

5. The medical device of claim 1, wherein the first interface is at least one probe.

6. The medical device of claim 1, wherein the connector further comprises a jet connector configured to connect to a fluid supply to provide fluid to a jet opening of the medical device.

7. The medical device of claim 1, wherein the connector further comprises an electric connector configured to connect electronics components of the medical device to a main control unit to provide electricity to the electronics components of the medical device.

8. The medical device of claim 1, wherein the connector further comprises a gas channel configured to provide gas flow to the medical device.

9. The medical device of claim 1, wherein the connector further comprises a light guide pin.

10. The medical device of claim 1, wherein the first region further comprises a light guide pin and a gas channel.

11. The medical device of claim 10, wherein the first interface includes a coaxial probe interface having a spring-loaded signal pin that compresses upon coupling with a complementary pad of a control unit.

12. The medical device of claim 11, wherein the second interface is a multi-pin interface configured to transmit analog signals captured by a sensor of the medical device.

13. The medical device of claim 1, wherein the first region further comprises a light guide and a gas channel, wherein the first interface is a first pad, a second pad and a third pad positioned circumferentially around at least one of the light guide and the gas channel.

14. A medical device comprising:
   a cable extending longitudinally from a distal end to a proximal end;
   an image sensor; and
   a connector at the proximal end of the cable, the connector comprising:
      a first region, wherein the first region comprises a first interface configured to transmit a first set of video data signals; and
      a second region spaced from the first region, wherein the second region comprises a second interface configured to transmit a second set of video data signals having a second bandwidth of 0.5 GHz or less.

15. The medical device of claim 14, wherein the first bandwidth is more than 1 GHz.

16. The medical device of claim 15, wherein the first interface is at least one probe configured to abut a pad of a control unit receptacle.

17. The medical device of claim 14, wherein the second interface comprises a multi-pin interface.

18. The medical device of claim 14, wherein the first region further comprises a light guide pin and a gas channel.

19. The medical device of claim 18, wherein the first interface includes a coaxial probe interface having a spring-loaded signal pin that compresses upon coupling with a complementary pad of a control unit.

20. A medical device comprising:
   a cable extending longitudinally from a distal end to a proximal end; and
   a connector at the proximal end of the cable, the connector comprising:
      a first region, wherein the first region comprises a first interface configured to transmit a first set of video data signals having a first bandwidth of more than 1 GHz; and
      a second region spaced from the first region, wherein the second region comprises a second interface configured to transmit a second set of video data signals having a second bandwidth of 0.5 GHz or less.

* * * * *